United States Patent [19]

Heinz et al.

[11] Patent Number: 5,226,874
[45] Date of Patent: Jul. 13, 1993

[54] ELECTROMECHANICAL BACK BRACE APPARATUS

[75] Inventors: Thomas J. Heinz, Flintridge; Thomas A. Walker, Ojai; Eric Plambeck, Ventura, all of Calif.

[73] Assignee: Bio-Cybernetics International, Pasadena, Calif.

[21] Appl. No.: 714,785

[22] Filed: Jun. 13, 1991

[51] Int. Cl.$^5$ .................... A61F 5/24; A61F 5/37
[52] U.S. Cl. .................... 602/19; 128/96.1; 128/101.1; 128/876
[58] Field of Search ................. 128/876, 384, 385, 63, 128/57-59, 101.1, 95.1, 96.1, 98.1, 99.1, 26, 25 R, 24.1-24.5, 900, 686, 677; 450/96, 146; 602/19, 32, 36, 40, 17, 18; 254/214, 216; 24/32

[56] References Cited

U.S. PATENT DOCUMENTS

| | | | |
|---|---|---|---|
| 2,754,817 | 7/1956 | Nemeth | 482/131 X |
| 3,095,873 | 7/1963 | Edmunds | 128/686 |
| 4,109,646 | 8/1978 | Keller | 128/686 |
| 4,206,765 | 6/1980 | Huber | 128/677 |
| 4,413,620 | 11/1983 | Tucker | 128/134 |
| 4,644,938 | 2/1987 | Yates et al. | 128/26 |
| 4,884,562 | 12/1989 | Stone | 128/78 |
| 5,062,414 | 11/1991 | Grim | 128/68.1 |

FOREIGN PATENT DOCUMENTS 0222636  11/1985  Japan ................... 24/32

Primary Examiner—Richard J. Apley
Assistant Examiner—John Leubecker
Attorney, Agent, or Firm—Nikaido Marmelstein Murray & Oram

[57] ABSTRACT

A corset-type back brace apparatus is disclosed which has electromechanical means for tightening a corset around the trunk of a patient to a desired tension. The electromechanical means includes a pair of motor driven rollers which are controllable by the patient to effect predetermined tension settings.

3 Claims, 2 Drawing Sheets

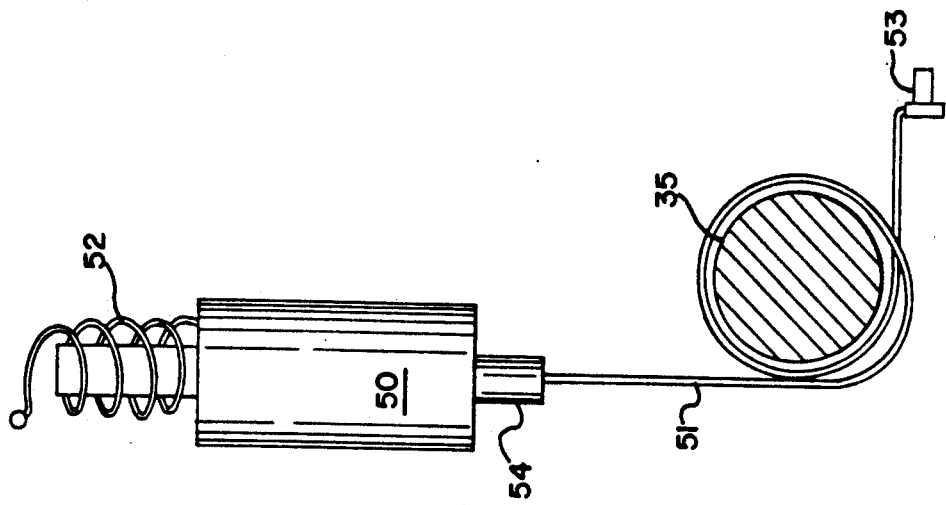
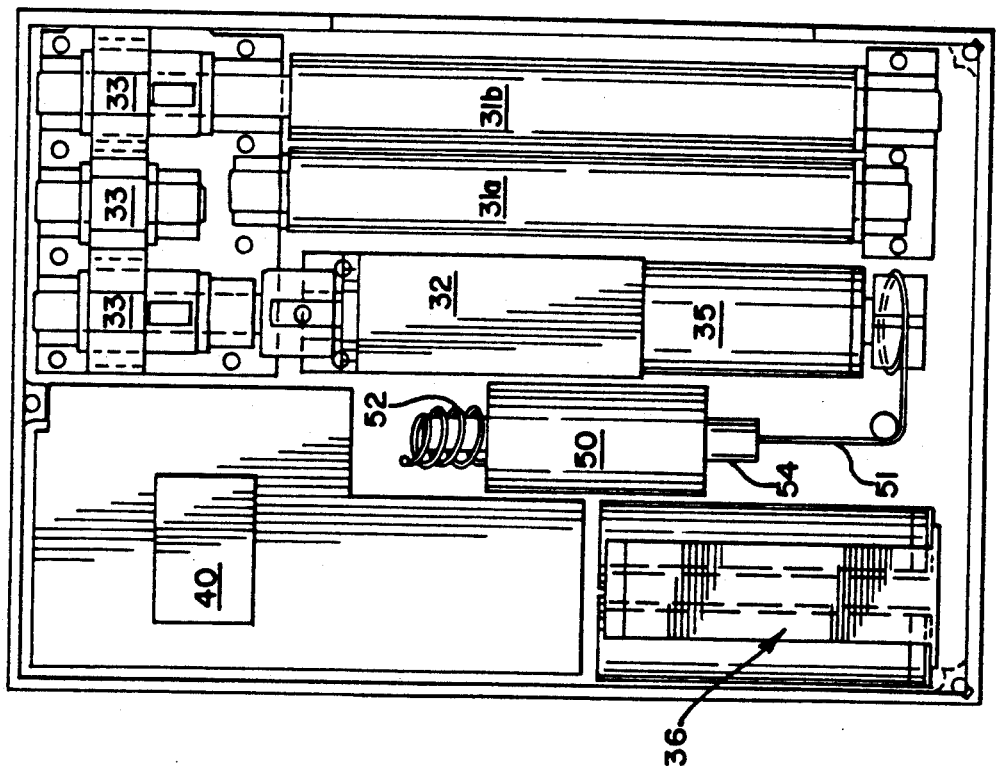

ELECTROMECHANICAL BACK BRACE APPARATUS

BACKGROUND OF THE INVENTION

A common method of alleviating pain and promoting healing in post-operative back surgery patients and those otherwise suffering from back injuries is to stabilize the spine by means of a brace. Such braces typically consist of a corset made of canvas or similar material which can be snugly fitted around the patient's trunk. The back portion of the corset will usually have pockets into which are inserted rigid stays for providing vertical support. Such braces are effective if worn properly, but most patients have difficulty manually adjusting the brace to a tight enough fit for providing adequate support. This is especially true in the case of post-operative patients who are in pain and lack sufficient strength. Such patient non-compliance obviously reduces the effectiveness of the brace. Another problem with these types of braces is their inability to adapt as the patient moves from a standing to a sitting position.

SUMMARY OF THE INVENTION

The present invention is a corset-type back brace which is tightened around a patient by means of a pair of motor driven rollers. The rollers and motor are mounted within a control module housing which also contains a microcomputer for controlling the operation of the motor. The microcomputer may also be appropriately programmed so that the corset is tightened to a predetermined setting, with separate settings for sitting and standing positions. The control module is attached to the corset by means of hook-and-loop fastener material which provides sufficient shear strength for holding the corset under tension but may be easily and quickly peeled off in the event of a malfunction. It is thus an object of the present invention to provide a back brace which may be tightened around a patient with little physical effort and which may be tightened automatically to a predetermined extent.

Other objects, features, and advantages of the invention will become evident in light of the following detailed description considered in conjunction with the referenced drawings of a preferred exemplary embodiment according to the present invention.

BRIEF DESCRIPTION OF THE DRAWINGS

FIG. 4 shows the internal components of the control module.
FIG. 5 is a schematic depiction of the operation of the solenoid brake.

DETAILED DESCRIPTION OF THE INVENTION

Figure 1:
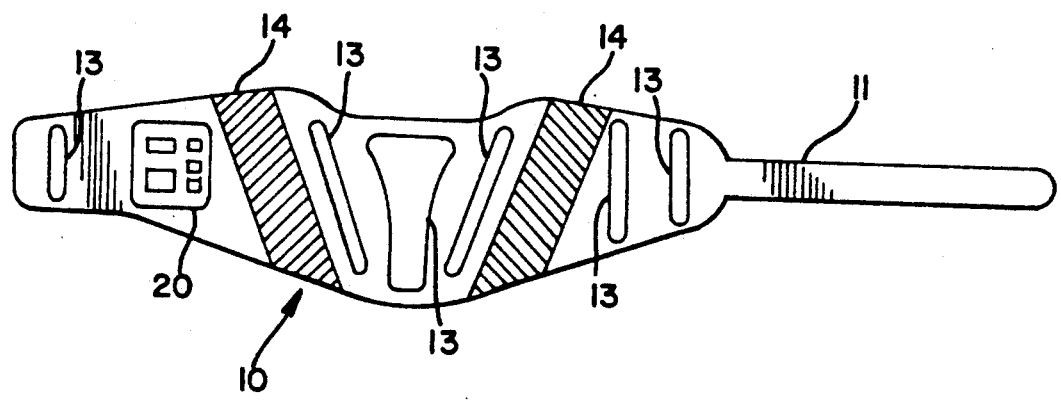
FIG. 1 shows the corset in its extended position.

The back brace in accordance with the present invention basically comprises a corset upon which is mounted a control module for tightening the corset around the trunk of a patient. FIG. 1 shows the corset 10 and with the control module housing 20 mounted thereon. The corset 10 is made of canvass or similar fabric with elastic portions 14 interspersed. A plurality of pockets 13 are provided into which may be inserted rigid stays for providing vertical support. The control module 20 is held in place on the corset 10 by means of hook-and-loop fastener material 15 (such as Velcro) affixed to the back of the control module and the corset. Such material is capable of withstanding a large amount of shear stress so that the corset may be kept under tension but can be easily peeled away should the apparatus malfunction. The tongue 11 is an extension of the corset 10 which is adapted for insertion into the control module.

Figure 2:
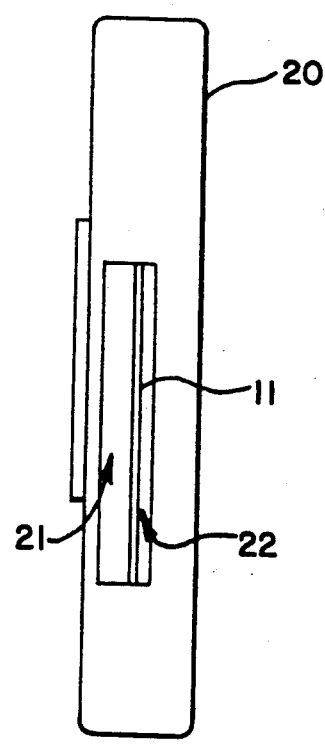
FIG. 2 is a side view of the control module.

FIG. 2 is a side view of the control module 20 showing the entrance and exit slots, 21 and 22, respectively, for the tongue. As is described more fully below, motor driven rollers within the control module housing act so as to pull the tongue 11 and thereby tighten the corset 10 around the trunk of the patient.

Figure 3:
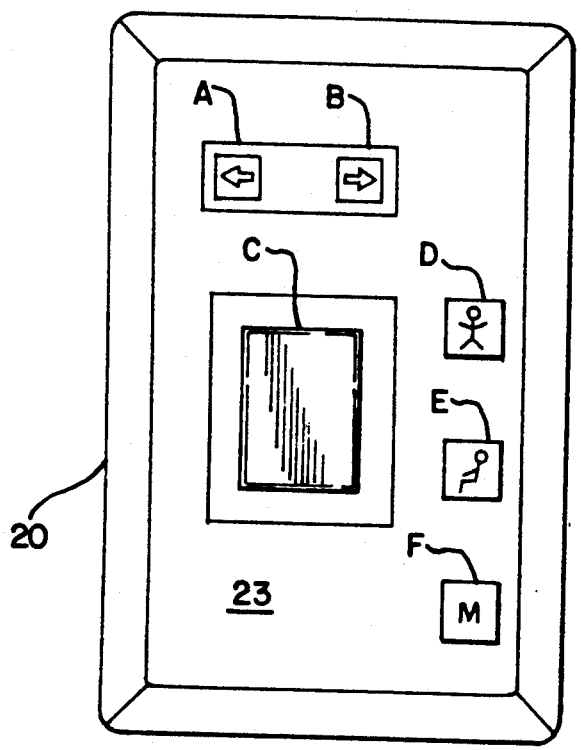
FIG. 3 shows the front of the control module.

FIG. 3 shows the front panel 23 of the control module where buttons are provided for controlling the operation of the apparatus. After the tongue 11 is inserted, buttons A and B loosen and tighten, respectively, the corset by causing the motor within the control module to drive the rollers in one direction or the other. During the tightening process, a microcomputer 40 counts the number of rotations made by the motor by inductively coupling the motor to the microcomputer's data input circuitry. That number of motor rotations, constitutes a setting for the brace and may be stored for later recall in the microcomputer's memory by the use of the memory button F. In another embodiment, the microcomputer monitors and stores the output of a strain gauge which measures the tension of the corset. To store a setting appropriate for the sitting position, button F is pressed in conjunction with button E. For the standing position, button F is pressed in conjunction with button D. To recall these settings, the patient presses either button D or E alone which causes the motor to rotate the stored number of times. In this way, a patient may easily adjust the setting of brace according to whether he is sitting or standing. A toggle button C is also provided for toggling between the sitting and standing positions.

FIG. 4 shows the internal components of the control module 20 which include pinch rollers 31a and 31b, reduction gears 32, translation gears 33, electric motor 35, power source 36, microcomputer 40, and solenoid 50. The tongue 11 is inserted between the pinch rollers 31a and 31b, rotation of which causes translational motion of the tongue to either tighten or loosen the corset.

Power source 36 consists of terminals to which are connected common alkaline batteries which supply power to motor 35. Motor 35 drives pinch roller 31b via reduction gear train 32 and translation gears 33. Reduction gear train 32 provides a 246:1 reduction ratio which not only gives a mechanical advantage to the motor 35 but also aids in the braking function as will be described below. Pinch roller 31a is an idler roller which serves to hold the tongue 11 firmly against driven pinch roller 31b.

The braking function serves to lock the tongue 11 in position when the desired setting is reached. Brake cable 51 is circumferentially wrapped around an end of the shaft of motor 35. As shown in FIGS. 4 and 5, one end of the brake cable 51 is fixed to the control module chassis by means of a screw 53. The other end of the brake cable 51 is attached to solenoid shaft 54, the latter being connected to the control module housing by means of spring 52. When the solenoid is unenergized, spring 52 holds cable 51 under tension in order to prevent rotation of the motor 35. This also effectively locks the pinch roller 31b which thereby holds the tongue 11 in position between the pinch rollers. Since the rotation of pinch roller 31b is coupled to the motor 35 via reduction gear train 32 with a 246:1 reduction ratio, pinch roller 31b is effectively locked even if slight rotation of the motor 35 should occur due to slippage of the motor shaft within brake cable 51. In order to release the brake, solenoid 50 is energized at the same time motor 35 is actuated. Energization of the solenoid 50 causes solenoid shaft 54 to pull away from the control module chassis and release the tension on cable 51 to allow free wheeling of the motor 35.

Although the invention has been described in conjunction with the foregoing specific embodiment, many alternatives, variations, and modifications will be apparent to those of ordinary skill in the art. Those alternatives, variations, and modifications are intended to fall within the scope of the following appended claims.

What is claimed is:

1. A back brace apparatus comprising:
   a corset adapted to be wrapped around the trunk of a patient, the corset having pockets for the insertion of rigid stays for providing vertical support;
   a control module housing detachably mounted on the corset by means of hook-and-loop fastener fabric affixed to the back of the control module housing and a portion of the corset;
   a motor mounted in said housing;
   a pair of pinch rollers within the control module housing for removably receiving a tongue of the corset therebetween, the pinch rollers being made to rotate in one direction or the other by the motor to thereby tighten or loosen the corset around the patient's trunk; and,
   control means for controlling the motor so that the corset is tightened to a predetermined setting comprising
   means for counting the number of revolutions made by the motor in tightening or loosening the corset; and,
   means for storing the number of revolutions counted by said counting means for recall by the control means.

2. The back brace as set forth in claim 1 further comprising a reduction gear train between the pinch rollers and the motor.

3. A back brace apparatus comprising:
   a corset adapted to be wrapped around the trunk of a patient, the corset having pockets for the insertion of rigid stays for providing vertical support;
   a control module housing detachably mounted on the corset by means of hook-and-loop fastener fabric affixed to the back of the control module housing and a portion of the corset;
   a motor mounted in said housing;
   a pair of pinch rollers within the control module housing for removably receiving a tongue of the corset therebetween, the pinch rollers being made to rotate in one direction or the other by the motor to thereby tighten or loosen the corset around the patient's trunk;
   control means for controlling the motor so that the corset is tightened to a predetermined setting; and,
   a brake cable having one end circumferentially wrapped around an end of a shaft of the motor and affixed to the control module housing, and the other end attached to a solenoid shaft.

* * * * *